(12) United States Patent
Jain et al.

(10) Patent No.: US 11,872,547 B2
(45) Date of Patent: Jan. 16, 2024

(54) PROCESS FOR THE PHOTOCATALYTIC ALLYLIC OXIDATION OF OLEFINS USING CARBON DIOXIDE

(71) Applicant: COUNCIL OF SCIENTIFIC & INDUSTRIAL RESEARCH, New Delhi (IN)

(72) Inventors: Suman Lata Jain, Dehradun (IN); Sandhya Saini, Dehradun (IN); Shafuir Rehman Khan, Dehradun (IN); Praveen Kumar Khatri, Dehradun (IN); Anjan Ray, Dehradun (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 17/703,483

(22) Filed: Mar. 24, 2022

(65) Prior Publication Data

US 2022/0314208 A1    Oct. 6, 2022

(30) Foreign Application Priority Data

Mar. 31, 2021  (IN) .............................. 202111014943

(51) Int. Cl.
*B01J 31/00* (2006.01)
*B01J 31/18* (2006.01)
(Continued)

(52) U.S. Cl.
CPC ............. *B01J 31/183* (2013.01); *B01J 21/18* (2013.01); *B01J 35/004* (2013.01); *C01B 32/40* (2017.08);
(Continued)

(58) Field of Classification Search
None
See application file for complete search history.

(56) References Cited

U.S. PATENT DOCUMENTS

| 5,872,157 A * | 2/1999 | DeSimone ........... C08G 65/007 522/184 |
| 6,384,251 B1 | 5/2002 | Marwah et al. |
| 2015/0099876 A1 * | 4/2015 | Chan ...................... C07C 29/48 568/910.5 |

FOREIGN PATENT DOCUMENTS

| CN | 103801294 A * | 5/2014 | |
| WO | WO-2016148558 A1 * | 9/2016 | .............. B01J 23/06 |

OTHER PUBLICATIONS

CN-103801294-A, English translation (Year: 2014).*
(Continued)

*Primary Examiner* — Stefanie J Cohen
(74) *Attorney, Agent, or Firm* — Norton Rose Fulbright US LLP

(57) ABSTRACT

The present invention relates to a novel method for photocatalytic oxidation of allylic C—H bonds present in alkenes containing at least three carbon atoms. In this newly disclosed method, such alkenes, when reacted with carbon dioxide ($CO_2$) in an organic solvent containing a catalyst comprising of a supported molecular complex of transition metal ions under conditions of ambient temperature and pressure using a readily available household LED lamp, yield oxygenated products. The developed method represents a unique way to use $CO_2$ as an oxygen transfer agent to unsaturated organic compounds along with the formation of CO as a co-product using light as an energy source.

14 Claims, 2 Drawing Sheets

(51) Int. Cl.
*B01J 35/00* (2006.01)
*B01J 21/18* (2006.01)
*C07C 29/48* (2006.01)
*C07C 45/50* (2006.01)
*C01B 32/40* (2017.01)

(52) U.S. Cl.
CPC ............. *C07C 29/48* (2013.01); *C07C 45/50* (2013.01); *B01J 2231/70* (2013.01); *B01J 2531/16* (2013.01)

(56) References Cited

OTHER PUBLICATIONS

WO-2016148558-A1, English translation (Year: 2016).*
Arigoni et al., "Selenium Dioxide Oxidations of Olefins. Trapping of the Allylic Seleninic Acid Intermediate as a Seleninolactone", *J. Am. Chem. Soc.*, 95(23): 7917-7919, 1973.
Bhalerao U, Rapoport H. "Stereochemistry of Allylic Oxidation with Selenium Dioxide. Stereospecific Oxidation of gem-Dimethyl Olefins", *Journal of the American Chemical Society*, 93(19): 4835-4840, 1971.
Gu L, Zhang Y. "Unexepcted $CO_2$ splitting reactions to form CO with N-heterocyclic carbenes as organocatalysts and aromatic aldehydes as oxygen acceptors", *J. Am. Chem. Soc.*, 132(3):914-915, 2010.
Nair et al., "NHC catalyzed transformation of aromatic aldehydes to acids by carbon dioxide: an unexpected reaction", *Org. Lett.*, 12(11):2653-2655, 2010.
Pearson et al., "Oxidation of alkenes to enones using tert-butyl hydroperoxide in the presence of chromium carbonyl catalysts", *Tetrahedron Letters*, 25(12): 1235-1238, 1984.
Salmond et al., "Allylic oxidation with 3,5-dimethylpyrazole. Chromium trioxide complex steroidal .DELTA.5-7-ketones", *J. Org. Chem.*, 43(10):2057-2059, 1978.
Stephenson L.M., Speth D.R. "Mechanism of Allylic Hydroxylation by Selenium Dioxide", *J. Org. Chem.*, 44(25): 4683-4689, 1979.
Yang Y, Lee JW. "Toward ideal carbon dioxide functionalization", *Chem Sci.*, 10(14):3905-3926, 2019.

* cited by examiner

PROCESS FOR THE PHOTOCATALYTIC ALLYLIC OXIDATION OF OLEFINS USING CARBON DIOXIDE

FIELD OF THE INVENTION

The present invention relates to a process for photocatalytic oxidation of allylic C—H bonds present in alkenes containing at least three carbon atoms. Disclosed process, such alkenes, when reacted with carbon dioxide ($CO_2$) in an organic solvent containing a catalyst comprising of a supported molecular complex of transition metal ions under conditions of ambient temperature and pressure using a readily available household LED lamp, yield oxygenated products. The developed method represents a unique way to use $CO_2$ as an to oxygen transfer agent to unsaturated organic compounds along with the formation of CO as a co-product using light as an energy source.

BACKGROUND OF THE INVENTION

Carbon dioxide ($CO_2$) concentration is continuously increasing in the earth's atmosphere, attributed mainly due to industrialization and excessive consumption of fossil fuels. Such atmospheric $CO_2$ increase is a major cause of climate change and is accompanied by global warming.

Among the various options known for carbon dioxide mitigation, chemical utilization of $CO_2$ to produce valuable chemicals has found considerable interest in recent years (Yang and Lee, Chem. Sci. 2019, 10,3905). However, one of the major challenges regarding $CO_2$ chemical utilization is the higher thermodynamic stability of the $CO_2$ molecule, due to which a significant amount of energy is required for the activation and conversion of $CO_2$ into value-added products. In thermal catalysis, the requirements of significantly elevated temperatures for $CO_2$ activation make these processes highly energy intensive and lead to catalyst deactivation as a result of coke formation typical of high temperature processes.

Single electron reduction of $CO_2$ through a photocatalytic approach is desirable because it is simple, uses mild operating conditions, and above all has the prospect of harnessing solar energy, which is cheap, clean, and essentially inexhaustible. Despite the fact that the photocatalytic conversion of $CO_2$ is technically simple, economically viable, and environmentally friendly, several constraints such as poor conversion of $CO_2$, high electron-hole recombination, and low adsorption/affinity of $CO_2$ with respect to photocatalysts have limited the practical applicability of this conversion approach prior to this invention. So far, a number of photocatalytic materials including metal oxides, mixed metal oxides, molecular complexes and heterojunctions have been explored for the photoreduction of $CO_2$ to chemicals such as CO, $CH_4$, $CH_3OH$ etc.

On the other hand, the use of $CO_2$ as an oxidant is rarely reported in the literature. In open literature (Zhang et al J. Am. Chem. Soc. 2010, 132, 3, 914-915; Menon et al Org. Lett. 2010, 12, 2653-2655), there are reports of the oxidation of aldehydes to corresponding acids using $CO_2$ as an oxidant in the presence of DBU as base and N-heterocyclic carbenes (NHCs) as catalysts at room temperature. Mechanistically, this report suggested the addition of aldehyde to N-heterocyclic carbene followed by addition of $CO_2$ to give corresponding hydroxy carboxylate that subsequently lost CO and hydroxide to afford corresponding acid.

To the best of our knowledge, there is no prior art on the use of $CO_2$ as an oxygen transfer reagent under photocatalytic conditions at ambient temperature and pressure along with the formation of CO as a co-product.

Allylic oxidation of olefins to corresponding α,β-unsaturated hydroxyl or carbonyl compounds is an important transformation having applications in many areas ranging from agricultural products to pharmaceuticals. Allylic oxidation reactions have traditionally been performed using a range of stoichiometric oxidants, for example, chromic acid & its derivatives, potassium permanganate, manganese dioxide, ruthenium compounds, selenium dioxide, copper and its compounds and selenium dioxide (see e.g., U.S. Pat. No. 6,384,251; Arigoni, D. et al. (1973) J. Am. Chem. Soc. 95(23):7917-7919; Rapoport, H. et al. (1971) J. Am. Chem. Soc. 93(19):4835-4840; Stephenson, L. M. et al. (1979) J. Org. Chem. 44(25):4683-4689; Pearson, A. J. et al. Tetrahedron Lett. (1984) 25:1235; Salmond, W. G. et al. (1978) "*Allylic Oxidation With 3,5-Dimethylpyrazole. Chromium Trioxide. Complex Steroidal. DELTA.5-7-Ketones*," J. Org. Chem. 43:2057-2059). Subsequently, a wide range of catalytic methods using transition metal catalysis has been reported with different oxidants, like t-butyl hydroperoxide (TBHP) and $O_2$. Most of these procedures are not environmentally friendly and typically suffer from one or more additional drawbacks such as unsatisfactory yields, use of large excess of the oxidant(s), harsh reaction conditions, use of toxic chemicals, generation of copious amount of toxic waste, use of expensive reagents etc. and therefore, are generally not industrially feasible processes for bulk production. Therefore, development of simple, environmentally benign, efficient allylic oxidation processes using alternate oxidants is an unmet industrial need.

OBJECTIVE OF THE INVENTION

The main object of the present invention is to provide a photocatalytic process for the selective oxidation of allylic C—H bonds in alkenes using $CO_2$ as oxidant under mild reaction conditions, which obviates the drawbacks of hitherto known methods as detailed above. Further, the present invention is the first reported method for the allylic oxidation using $CO_2$ as an oxidant via a photocatalytic route.

Another objective of the present invention is to provide a novel photocatalytic route for the selective preparation of α,β-unsaturated hydroxyl or carbonyl compounds.

Yet another objective of the present invention is to provide to a novel photocatalytic route for the allylic oxidation of olefins with the conversion in the range of 20-80%.

Yet another objective of the present invention is to provide a novel photocatalytic route for the allylic oxidation of olefins to give α,β-unsaturated hydroxyl or carbonyl compounds with >65% selectivity.

Yet another objective of the present invention is to provide a method for the selective allylic oxidation with $CO_2$ at atmospheric pressure of $CO_2$ in typically ambient temperature ranges of 15-40° C., preferably at about 25° C.

Yet another objective is to use a polar solvent for the invention, selected from water, alcohols—linear or branched, for instance methanol or isopropyl alcohol, acetonitrile or dimethylformamide or dimethyl sulfoxide or tetrahydrofuran, or mixtures thereof as may be appropriate, in particular pure acetonitrile.

Yet another objective of the present invention is to use a visible light source having wavelength (λ) greater than 420 nm or a broad spectrum of solar energy containing such wavelengths for the activation of the carbon dioxide under mild conditions.

Yet another objective of the present invention is to provide an economically viable method for the reduction of $CO_2$ to CO along with the simultaneous oxidation of alkenes using a low cost, non-precious metal in the form of molecular ligand-assisted transition metal ions such as nickel, cobalt or copper, more specifically copper.

Yet another objective of the present invention is to provide a method for the selective allylic oxidation with $CO_2$ using highly stable nitrogen-containing ligands based on moieties such as phthalocyanine, porphyrin, bipyridine, etc.

Yet another objective of the present invention is to provide a method for the selective allylic oxidation with $CO_2$ using a reusable photocatalyst by supporting the molecular complex on to the photoactive support matrix, preferably 2D carbon materials. As a further advantage, the recovered photocatalyst is easy to recycle without any specific regeneration protocol.

SUMMARY OF THE INVENTION

The present invention relates to an innovative photocatalytic process for oxidation of alkenes with $CO_2$ and a catalyst comprising of molecular organic ligand assisted metal ions such as cobalt, nickel or copper supported onto photoactive semiconducting supports in the presence of an organic solvent in the temperature range 20-40° C. for a period of ranging from 10-30 h in a batch photoreactor using a house hold visible light to obtain desired oxidized products in the range 40-80% with >65% selectivity of corresponding $\alpha,\beta$-unsaturated hydroxyl or carbonyl compound. After the consumption of $CO_2$, the catalyst could be recovered from the reaction mixture and reused.

The present invention represents the first photocatalytic methodology for the oxidation of olefins with $CO_2$ to produce oxidized compounds of general formula I, II & III (Scheme 1), under ambient temperature and pressure (1 atm) conditions.

Yet another embodiment of the present invention is to provide to a novel photocatalytic route for the allylic oxidation of olefins with the conversion in the range of 20-80%.

Yet another embodiment of the present invention is to provide a novel photocatalytic route for the allylic oxidation of olefins at atmospheric pressure of $CO_2$ in typically ambient temperature ranges of 15-40° C., preferably at about 25° C.

Yet another embodiment of the present invention is to provide to a novel photocatalytic route for the allylic oxidation of olefins with $CO_2$ to give $\alpha,\beta$-unsaturated hydroxyl or carbonyl compounds in >65% selectivity.

Yet another embodiment of the present invention is to provide to a novel photocatalytic route for the simultaneous production of CO from $CO_2$ along with the oxygen transfer to the allylic C—H of olefin molecule.

In another preferred embodiment, the polar solvent of the invention is selected from water, alcohol-linear or branched selected from methanol or isopropyl alcohol, acetonitrile or dimethylformamide or dimethyl sulfoxide or tetrahydrofuran, preferably acetonitrile.

In another embodiment of the present invention, transition metal based photocatalyst is a macrocyclic chelated complex of cobalt, nickel, copper etc selected from the group consisting of phthalocyanine, porphyrin, polypyridyl etc., preferentially polypyridyl complex of copper ions.

In another embodiment of the present invention the metal complex can be supported to a photoactive semiconducting support that is selected from the group consisting of 2D carbon materials, heteroatom doped carbon, transition metal oxides or mixed metal oxides, preferably 2D carbon materials such as graphene oxide and its derivatives.

In a more preferred embodiment of the catalyst, the copper complex is loaded on the support in the range of 2-20 wt % and the loading of copper in the synthesized catalyst is determined by inductive coupled plasma atomic emission spectroscopy (ICP-AES).

In yet another embodiment of the present invention, the amount of photocatalyst used is preferably in the range of 0.1 to 5 mol %, preferably 1 mol %, relative to the starting olefin.

In yet another embodiment of the present invention, the reaction time is preferably in the range of 10-30 h.

In yet another embodiment of the present invention, the catalyst was recovered after the reaction by filtration or centrifugation.

In yet another embodiment of the present invention, the visible light source used is preferably house hold LED light of 10 to 30 W.

In another embodiment of the present invention, the conversion of the olefin is analyzed by GC-FID on the basis of the unreacted substrate.

In another embodiment of the present invention, the identification of the oxidized products is done by GC-MS.

In another embodiment of the present invention, the oxidized products are isolated by column chromatography using silica gel as a column bed.

In another embodiment of the present invention, the formation of CO in the gaseous effluent is determined by refinery gas analyzer (RGA) technique.

Table: 1 enlists the various exemplary embodiments of the process of the invention, wherein the starting substrates are readily available.

The invention will now be described in detail in connection with certain preferred and optional embodiments, so that various aspects thereof may be more fully understood and appreciated.

DETAILED DESCRIPTION OF THE INVENTION

Definitions

Figure 1:
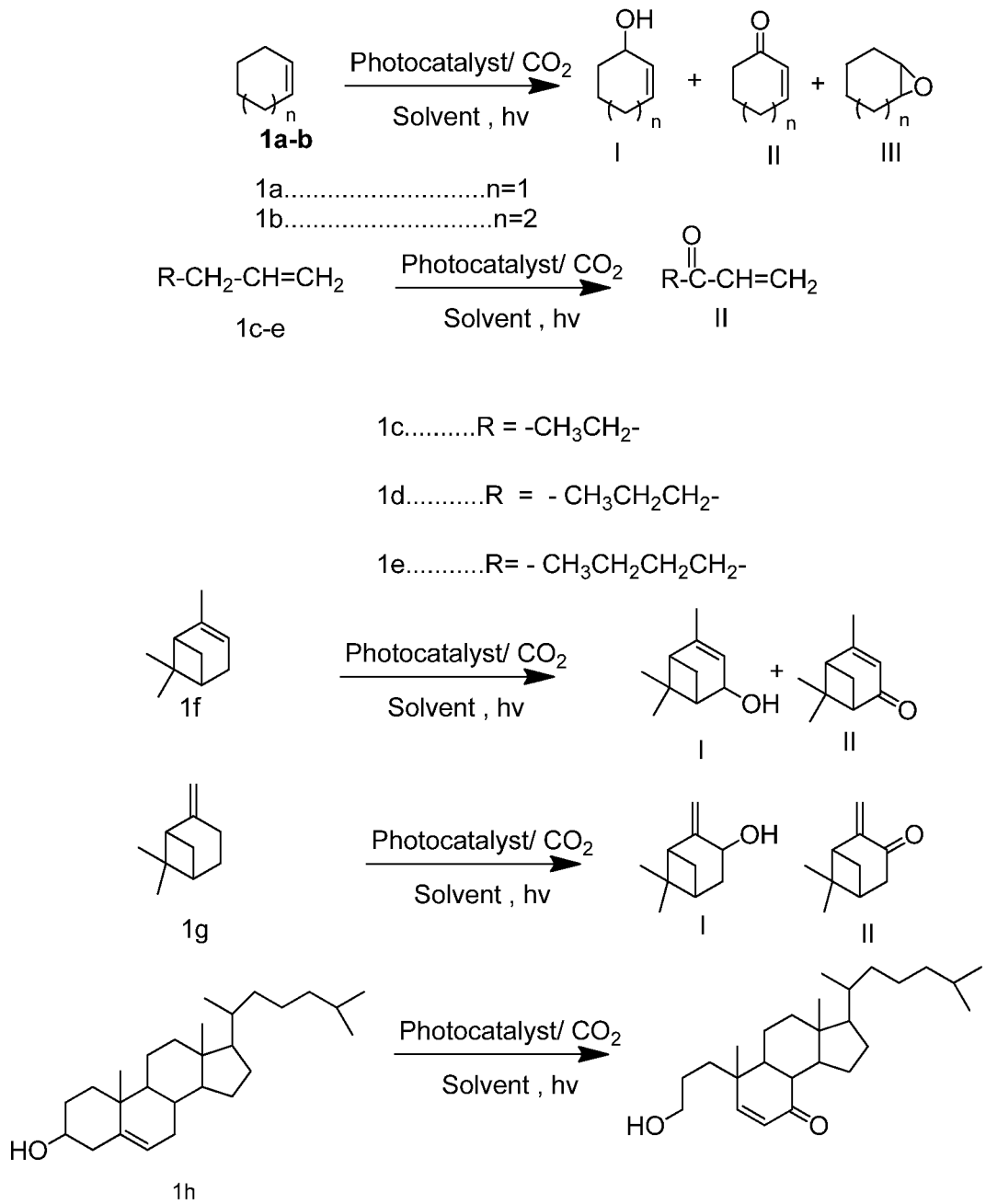
FIG. 1: Chemical synthesis, structure and formula of the substrates.
Figure 2:
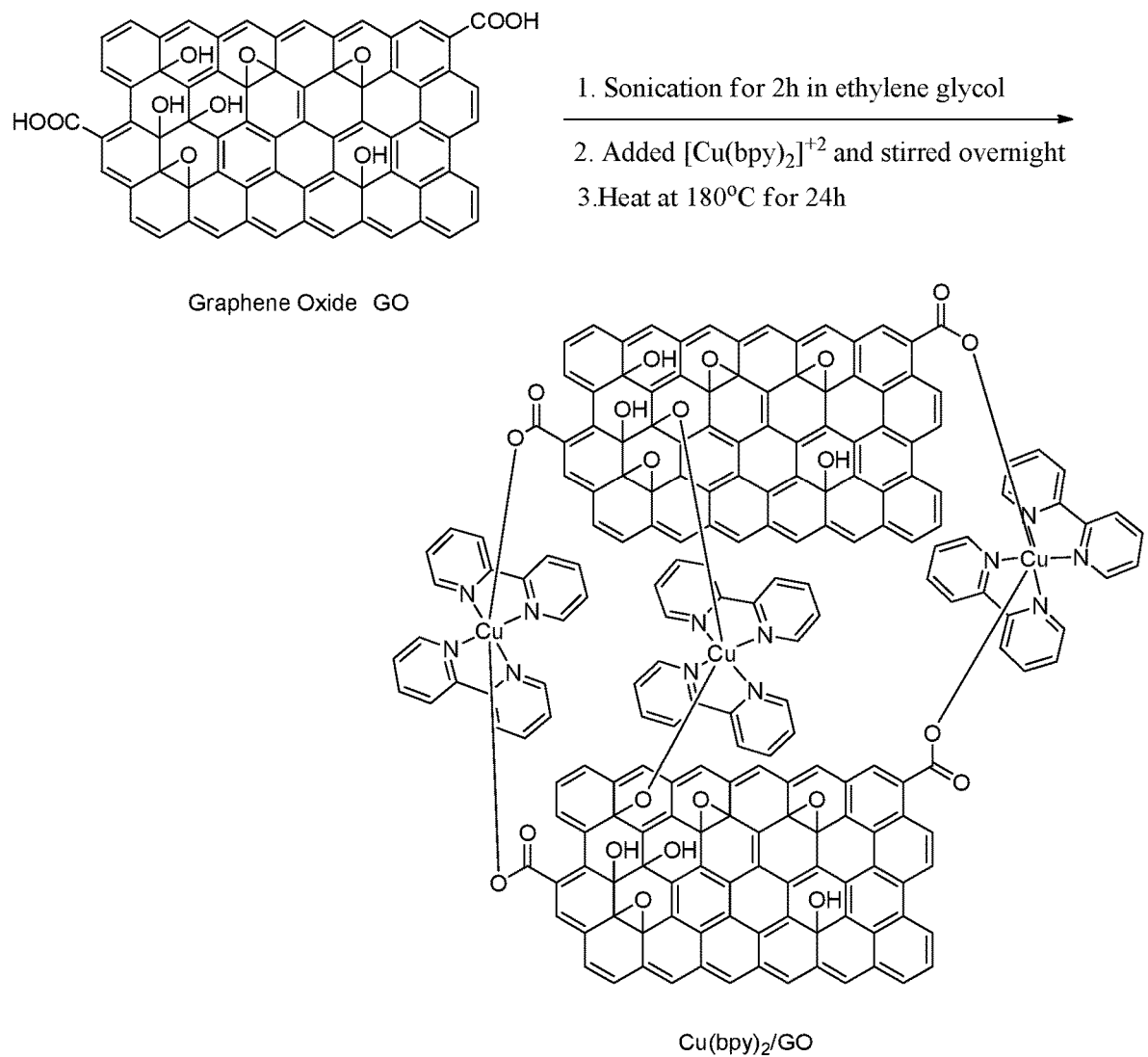
FIG. 2: Chemical synthesis and structure of the photocatalyst.

The process comprises reacting an olefin having an unhindered allylic C—H bond with carbon dioxide in the presence of a photocatalyst consisting of molecular organic ligand assisted metal ions and a polar organic solvent at temperature ranging from 20 to 40° C. and at atmospheric pressure under the visible light irradiation to prepare the corresponding $\alpha,\beta$-unsaturated hydroxyl or carbonyl compounds selectively.

As utilized herein including in the claims "allylic oxidation" means oxidation of an allylic compound by replacing the allylic hydrogens with oxygen derived from $CO_2$.

As utilized herein including in the claims "reactants" collectively references both alkene and $CO_2$ (oxidant). Solvents including both aqueous and organic solvents and the hybrid photocatalyst are a combination of molecular complex attached with a photoactive support.

Within this disclosure, "visible light" means light having a wavelength (λ) greater than 420 nm.

In a preferred embodiment of this invention, any olefin having an unhindered allylic C—H bond can be employed in the process described by this invention. Mono-olefins, whether cyclic or acyclic—whether linear or branched—are preferred, but bicyclic or inactivated olefins such as terpenes and olefins having pharmaceutical importance such as Δ5 steroids can also be employed. Most of the aforementioned olefin types are available commercially and used as received.

Consstituents
Olefins

The olefin used in the present invention a simple hydrocarbon containing only carbon and hydrogen atoms. Non-limiting examples of olefins which are suitable for the process of this invention include 1-hexene, 2-hexene, 1-heptene, 2-methylpentene, cyclohexene, cycloheptene and analogously, the various isomers of the mentioned olefins, as well as bicyclic olefins such as β-pinene, limonene and their substituted variants.

Oxidant (Carbon Dioxide)

In the present invention carbon dioxide is used to allylically oxidize olefins in the presence of a photocatalyst under visible illumination. Carbon dioxide, among the two oxygen atoms transferred one oxygen atom to the allylic C—H position and converted to carbon monoxide during the process. The reaction mixture containing substrate, solvent and photocatalyst was either saturated with $CO_2$ or purged continuously with $CO_2$ flow for effective oxidation.

Organic Solvents

Substrates (olefins and $CO_2$) used in the present invention are preferably dissolved in organic solvents. Specifically polar organic solvents were used mainly due to the higher solubility of $CO_2$ in polar solvents. Suitable organic solvents include specifically, but not limited to dimethylformamide (DMF), dimethylacetamide (DMA), acetonitrile (ACN), dimethyl sulfoxide (DMSO) and N-methyl pyrrolidone (NMP) or mixtures thereof.

Photocatalyst

Suitable photocatalyst effective for catalyzing the allylic oxidation in accordance with the present invention is a hybrid photocatalyst consisting of a chelated copper complex supported on a 2D carbon structure. Examples of suitable copper complexes include, specifically but not exclusively, copper (II) bipyridine, copper (II) phthalocyanine, copper (II) Schiff base supported on a photoactive support which consists of a functionalized carbon network that provide active sites for stable anchoring of the metal complex to prevent metal leaching during the photoreaction. The copper complexes and photoactive supports were prepared by following well-documented literature protocols. The supported hybrid catalysts are highly stable they remain intact during the oxidation process and can be easily recovered and reused.

EXAMPLES

Following examples are given by way of illustration and therefore should not be construed to limit the scope of the invention.

Example 1-19

Various olefins (1a-1h) were oxidized in accordance with the standard protocol set forth above and the results of these experiments are summarized in Table 1.

Example 1:—General Procedure for the Oxidation of Cyclohexene

Cyclohexene (1a) and polar organic solvent, preferably acetonitrile in (1:2 to 1:10 weight ratio with respect to the substrate) was taken in to a 60 ml vessel. Further, the hybrid photocatalyst (1 to 10 mol % of the substrate) was added and the resulting mixture was saturated with $CO_2$ by purging at 1 atm pressure. The reaction vessel was sealed and irradiated with 20 W LED light (Model No. HP-FL-20 W-F, Hope LED Opto-Electric CO., Ltd) for 24 h. The intensity of the LED light at the reaction flask was measured to be 86 $W/m^2$ by intensity meter. The conversion of the olefin was examined by GC-FID based on the unreacted substrate. The selectivity of the α,β-unsaturated hydroxyl or carbonyl compounds was determined by GC-MS. The formation of CO along with the minute amount of hydrogen in the gaseous phase was confirmed by Residual Gas Analysis (RGA). Furthermore, after the reaction, the catalyst was recovered by filtration and any unreacted olefin and solvent were recovered by distillation under reduced pressure. The resulting residue was subjected to column chromatography to isolate the products. The conversion of olefin was consistently in the range of 40-80% and the selectivity towards the corresponding α,β-unsaturated hydroxyl and ketone remained >65%.

Example 2: Oxidation of Cyclohexene Using Molecular Copper Complex as Catalyst

Cyclohexene (1a) and polar organic solvent, preferably acetonitrile in (1:2 to 1:10 weight ratio with respect to the substrate) was taken in to a 60 ml vessel. Further, the copper complex (1 to 10 mol % of the substrate) was added and the resulting mixture was saturated with $CO_2$ by purging at 1 atm pressure. The reaction vessel was sealed and irradiated with 20 W LED light (Model No. HP-FL-20 W-F, Hope LED Opto-Electric CO., Ltd) for 24 h. The intensity of the LED light at the reaction flask was measured to be 86 $W/m^2$ by intensity meter. The conversion of the olefin was examined by GC-FID based on the unreacted substrate. There was no reaction occurred using homogeneous complex under otherwise identical conditions.

Example 3: Oxidation of Cyclohexene Using Bare Graphene Oxide as Catalyst

Cyclohexene (1a) and polar organic solvent, preferably acetonitrile in (1:2 to 1:10 weight ratio with respect to the substrate) was taken in to a 60 ml vessel. Further, the bare graphene oxide as photocatalyst (1 to 10 mol % of the substrate) was added and the resulting mixture was saturated with $CO_2$ by purging at 1 atm pressure. The reaction vessel was sealed and irradiated with 20 W LED light (Model No. HP-FL-20 W-F, Hope LED Opto-Electric CO., Ltd) for 24 h. The intensity of the LED light at the reaction flask was measured to be 86 $W/m^2$ by intensity meter. The conversion of the olefin was examined by GC-FID based on the unreacted substrate. The selectivity of the α,β-unsaturated hydroxyl or carbonyl compounds was determined by GC-MS. The conversion of olefin and the selectivity towards the corresponding α,β-unsaturated hydroxyl and ketone is given in the Table 1, entry 3.

Example 4: Oxidation of Cyclohexene in the Dark

Cyclohexene (1a) and polar organic solvent, preferably acetonitrile in (1:2 to 1:10 weight ratio with respect to the substrate) was taken in to a 60 ml vessel. Further, the hybrid photocatalyst (1 to 10 mol % of the substrate) was added and the resulting mixture was saturated with $CO_2$ by purging at 1 atm pressure. The reaction vessel was sealed and kept in the dark condition under continuous stirring. The conversion of the olefin was examined by GC-FID based on the unreacted substrate. There was no conversion observed that illustrates that visible illumination was essential for the oxidation.

Example 5: Oxidation of Cyclohexene in the Absence of Catalyst

Cyclohexene (1a) and polar organic solvent, preferably acetonitrile in (1:2 to 1:10 weight ratio with respect to the substrate) was taken in to a 60 ml vessel. The reaction vessel was sealed and irradiated with 20 W LED light (Model No. HP-FL-20 W-F, Hope LED Opto-Electric CO., Ltd) for 24 h. The intensity of the LED light at the reaction flask was measured to be 86 $W/m^2$ by intensity meter. There was no conversion observed as ascertained by GC-FID, which illustrated that presence of photocatalyst was essential for the oxidation with $CO_2$ (Table 1, entry 5)

Example 6: Oxidation of Cyclohexene Using Recovered Catalyst (Recycling Experiment-1)

Cyclohexene (1a) and polar organic solvent, preferably acetonitrile in (1:2 to 1:10 weight ratio with respect to the substrate) was taken in to a 60 ml vessel. Further, the recovered photocatalyst from experiment 1 was added and the resulting mixture was saturated with $CO_2$ by purging at 1 atm pressure. The reaction vessel was sealed and irradiated with 20 W LED light (Model No. HP-FL-20 W-F, Hope LED Opto-Electric CO., Ltd) for 24 h. The conversion of the olefin and selectivity of the α,β-unsaturated hydroxyl or carbonyl compound as determined by GC-FID and GC-MS is mentioned in the Table 1 (entry 6).

Example 7: Oxidation of Cyclohexene Using Recovered Catalyst (Recycling Experiment-2)

Cyclohexene (1a) and polar organic solvent, preferably acetonitrile in (1:2 to 1:10 weight ratio with respect to the substrate) was taken in to a 60 ml vessel. Further, the recovered photocatalyst from experiment 6, was added and the resulting mixture was saturated with $CO_2$ by purging at 1 atm pressure. The reaction vessel was sealed and irradiated with 20 W LED light (Model No. HP-FL-20 W-F, Hope LED Opto-Electric CO., Ltd) for 24 h. The conversion of the olefin and selectivity of the α,β-unsaturated hydroxyl or carbonyl compound as determined by GC-FID and GC-MS is mentioned in the Table 1 (entry 7).

Example 8-13: Oxidation of Cyclohexene Using Different Solvents

Cyclohexene (1a) and polar organic solvent (as mentioned in Table 1) in (1:2 to 1:10 weight ratio with respect to the substrate) was taken in to a 60 ml vessel. Further, the hybrid photocatalyst was added and the resulting mixture was saturated with $CO_2$ by purging at 1 atm pressure. The reaction vessel was sealed and irradiated with 20 W LED light (Model No. HP-FL-20 W-F, Hope LED Opto-Electric CO., Ltd) for 24 h. The conversion of the olefin and selectivity of the α,β-unsaturated hydroxyl or carbonyl compound as determined by GC-FID and GC-MS is mentioned in the Table 1 (entry 8-13).

Example 14-19: Oxidation of Different Olefins Under Optimized Conditions

Olefin (1b-1h) and polar organic solvent, preferably acetonitrile in (1:2 to 1:10 weight ratio with respect to the substrate) was taken in to a 60 ml vessel. Further, the hybrid photocatalyst (1 to 10 mol % of the substrate) was added and the resulting mixture was saturated with $CO_2$ by purging at 1 atm pressure. The reaction vessel was sealed and irradiated with 20 W LED light (Model No. HP-FL-20 W-F, Hope LED Opto-Electric CO., Ltd) for 24 h. The intensity of the LED light at the reaction flask was measured to be 86 $W/m^2$ by intensity meter. The conversion of the olefin was examined by GC-FID based on the unreacted substrate. The selectivity of the α,β-unsaturated hydroxyl or carbonyl compounds was determined by GC-MS. The results obtained for the conversion of olefin and the selectivity towards the corresponding α,β-unsaturated hydroxyl and ketone is summarized in Table 1, entry 14-19.

TABLE 1

Photocatalytic allylic oxidation of alkenes with $CO_2$

| Example | Olefin | Photocatalyst | Light | Solvent | Conv. (%)[b] | Product Select. (%)[c] | | |
|---|---|---|---|---|---|---|---|---|
| | | | | | | I | II | III |
| 1 | 1a | Cu(bpy)$_2$/GO | Yes | CH$_3$CN | 65 | 35 | 60 | 5 |
| 2 | 1a | Cu(bpy)$_2$ | Yes | CH$_3$CN | — | — | — | — |
| 3 | 1a | GO | Yes | CH$_3$CN | 15 | 30 | 55 | — |
| 4 | 1a | Cu(bpy)$_2$/GO | No | CH$_3$CN | — | — | — | — |
| 5 | 1a | — | Yes | CH$_3$CN | — | — | — | — |
| 6 | 1a | Cu(bpy)$_2$/GO* | Yes | CH$_3$CN | 65 | 35 | 60 | 5 |
| 7 | 1a | Cu(bpy)$_2$/GO* | Yes | CH$_3$CN | 65 | 32 | 58 | 6 |
| 8 | 1a | Cu(bpy)$_2$/GO | Yes | DMA | 25 | 15 | 30 | 5 |
| 9 | 1a | Cu(bpy)$_2$/GO | Yes | DMF | 30 | 15 | 25 | 4 |
| 10 | 1a | Cu(bpy)$_2$/GO | Yes | DMSO | 20 | — | — | 5 |
| 11 | 1a | Cu(bpy)$_2$/GO | Yes | NMP | 15 | — | — | — |
| 12 | 1a | Cu(bpy)$_2$/GO | Yes | H$_2$O | 20 | — | — | Trace |
| 13 | 1b | Cu(bpy)$_2$/GO | Yes | CH$_3$CN | 60 | 28 | 35 | 8 |
| 14 | 1c | Cu(bpy)$_2$/GO | Yes | CH$_3$CN | 75 | — | 94 | 6 |
| 15 | 1d | Cu(bpy)$_2$/GO | Yes | CH$_3$CN | 65 | — | 90 | — |
| 16 | 1e | Cu(bpy)$_2$/GO | Yes | CH$_3$CN | 54 | — | 90 | — |
| 17 | 1f | Cu(bpy)$_2$/GO | Yes | CH$_3$CN | 40 | 30 | 60 | — |
| 18 | 1g | Cu(bpy)$_2$/GO | Yes | CH$_3$CN | 37 | 32 | 54 | — |
| 19 | 1h | Cu(bpy)$_2$/GO | Yes | CH$_3$CN | 45 | — | 85 | — |

*Using recovered photocatalyst;
[a] determined by GC-FID;
[b] determined by GC-MS Observations The best results were obtained with the hybrid photocatalyst; whereas there was no reaction occurred in the presence of homogeneous copper complex as catalyst. Among the various organic solvents, acetonitrile exhibited best performance in terms of conversion of olefin and selectivity of the desired allylic oxidized compounds. The light irradiation was found to be essential and there was no reaction occurred under dark conditions in the absence of light. The use of bare support afforded a poor conversion with the selective formation of allylic hydroxyl compound. In addition, the use of hybrid photocatalyst offered facile recovery of the catalyst after the reaction by simple filtration and showed almost consistent efficiency at least for three recycles under similar conditions.

Advantages of the Invention

The various advantages of the present process are given below.

The present invention discloses the first photocatalytic oxidation using $CO_2$ as an oxidant under ambient temperature and pressure conditions. The use of $CO_2$ as an oxidant offers several advantages as it is abundantly available, safe, and inexpensive; also, it provided carbon monoxide, an important building block as a co-product during the oxidation process.

The present process serves monocyclic olefins (cyclohexene and cycloheptene) as substrates allylic oxidation products α,β-unsaturated hydroxyl, or carbonyl compounds obtained in higher yield. Unhindered chain olefins (1-hexene, 1-heptene and 1-octene) showed maximum conversion with the selective formation of the corresponding α,β-unsaturated ketones.

The present invention provides a unique approach for the oxidation of olefins and many other organic substrates that are not exemplified here using $CO_2$ as an oxidant.

We claim:

1. A process for photocatalytic allylic oxidation of olefins using carbon dioxide comprising the step of:
   a) oxidizing an allylic compound with 1 atmospheric pressure of $CO_2$ dissolved in a polar organic solvent in the presence of a supported copper catalyst under light irradiation at a temperature in the range of 15-35° C. for 12-30 hours irradiation time to obtain a corresponding oxidized product having conversion ranging from 40-80%, and selectivity >65% for an allylic hydroxy or a carbonyl compound along with the formation of carbon monoxide as a co-product in a gaseous phase.

2. The process as claimed in claim 1, wherein the light irradiation is done by using any light source having wavelength λ greater than 420 nm.

3. The process as claimed in claim 2, wherein the light irradiation is done by using a household LED light of 15-30 W.

4. The process as claimed in claim 1, wherein the allylic compound is an olefin having an unhindered allylic C—H bond and the olefin is selected from the group consisting of cyclic or chain or bicyclic monoolefin or compound having unhindered allylic position.

5. The process as claimed in claim 1, wherein the process is carried out in an organic solvent selected from the group consisting of acetonitrile, dimethylformamide (DMF), N,N-dimethylacetamide (DMA), N-methylpyrrollidone (NMP), dimethyl imidazoline (DMI), dimethyl sulfoxide and water.

6. The process as claimed in claim 5, wherein the organic solvent is acetonitrile.

7. The process as claimed in claim 1, wherein the photocatalyst is a combination of a copper complex with a photoactive carbon support.

8. The process as claimed in claim 1, wherein copper complex is selected from the group consisting of copper (II) bipyridine, copper (II) phthalocyanine, copper (II) porphyrin and copper (II) Schiff base.

9. The process as claimed in claim 8, wherein the copper complex is a copper (II) bipyridine complex.

10. The process as claimed in claim 1, wherein the photoactive carbon support is selected from the group consisting of graphene oxide or its functionalized variants.

11. The process as claimed in claim 1, wherein effective reaction time is ranging from 10 to 30 hrs.

12. The process as claimed in claim 1, wherein the photocatalyst is recovered by simple filtration or centrifugation.

13. The process as claimed in claim 1, wherein conversion of olefin is determined by GC-FID and selectivity of the oxidized product is determined by GC-MS.

14. The process as claimed in claim 12, wherein the photocatalyst is reused for oxidation of olefins.

* * * * *